United States Patent
Cook et al.

[11] Patent Number: 5,964,806
[45] Date of Patent: Oct. 12, 1999

[54] ADJUSTABLE IMPLANTABLE GENITOURINARY DEVICE

[75] Inventors: Timothy C. Cook, Wayzata; John H. Burton, Minnetonka, both of Minn.

[73] Assignee: UroMedica, Inc., Minnetonka, Minn.

[21] Appl. No.: 08/928,946

[22] Filed: Sep. 12, 1997

Related U.S. Application Data

[63] Continuation-in-part of application No. 08/873,444, Jun. 12, 1997.

[51] Int. Cl.$^6$ ............................... A61F 2/08; A61F 2/04; A61F 2/02; A61M 29/00
[52] U.S. Cl. ................................ 623/14; 623/11; 623/12; 600/30; 606/264; 606/191; 606/192; 604/54; 604/104; 604/201; 604/240
[58] Field of Search ................................ 623/11, 12, 14, 623/1, 66; 128/897, 898; 600/30; 606/264, 191–195, 108; 604/54, 96–99, 104, 164, 201, 215, 240, 264

[56] References Cited

U.S. PATENT DOCUMENTS

| | | | |
|---|---|---|---|
| 4,553,959 | 11/1985 | Hickey et al. | 604/96 |
| 4,559,043 | 12/1985 | Whitehouse et al. | 604/201 |
| 4,773,393 | 9/1988 | Haber et al. | 600/30 |
| 4,802,479 | 2/1989 | Haber et al. | 128/344 |
| 4,817,637 | 4/1989 | Hillegass et al. | 128/899 |
| 4,832,680 | 5/1989 | Haber et al. | 600/31 |
| 4,969,474 | 11/1990 | Schwarz | 128/885 |
| 5,012,822 | 5/1991 | Schwarz | 128/885 |
| 5,064,434 | 11/1991 | Haber | 623/11 |
| 5,097,848 | 3/1992 | Schwarz | 128/885 |
| 5,112,303 | 5/1992 | Pudenz et al. | 604/49 |
| 5,123,428 | 6/1992 | Schwarz | 128/885 |
| 5,181,921 | 1/1993 | Makita et al. | 606/195 |
| 5,304,123 | 4/1994 | Atala et al. | 604/54 |
| 5,334,153 | 8/1994 | McIntyre et al. | 604/99 |
| 5,383,896 | 1/1995 | Gershony et al. | 606/213 |
| 5,411,475 | 5/1995 | Atala et al. | 604/54 |
| 5,437,603 | 8/1995 | Cerny et al. | 600/29 |
| 5,499,994 | 3/1996 | Tihon et al. | 606/192 |
| 5,575,771 | 11/1996 | Walinsky | 604/96 |
| 5,578,009 | 11/1996 | Kraus et al. | 604/96 |
| 5,634,877 | 6/1997 | Salama | 600/29 |
| 5,637,074 | 6/1997 | Andino et al. | 600/29 |
| 5,830,228 | 11/1998 | Knapp et al. | 606/195 |

FOREIGN PATENT DOCUMENTS

| | | |
|---|---|---|
| 0784987 2 | 7/1997 | European Pat. Off. . |
| WO91/00069 | 1/1991 | WIPO . |

*Primary Examiner*—Mickey Yu
*Assistant Examiner*—Dinh X. Nguyen
*Attorney, Agent, or Firm*—Schwegman, Lundberg, Woessner, and Kluth, P.A.

[57] ABSTRACT

An implantable medical device and method for adjustably restricting a selected body lumen such as a urethra or ureter of a patient to treat urinary incontinence or ureteral reflux. The device includes an adjustable, self-sealing element having a continuous wall, including an inner surface defining a chamber. The adjustable element expands or contracts due to fluid volume introduced into the chamber for restricting a body lumen. After being implanted into a patient, the size of the adjustable element is altered by first locating the adjustable element implanted adjacent the body lumen, and then establishing fluid communication with the adjustable element. The volume of the adjustable element is then adjusted by either introducing or removing volume from the chamber of the adjustable element.

36 Claims, 12 Drawing Sheets

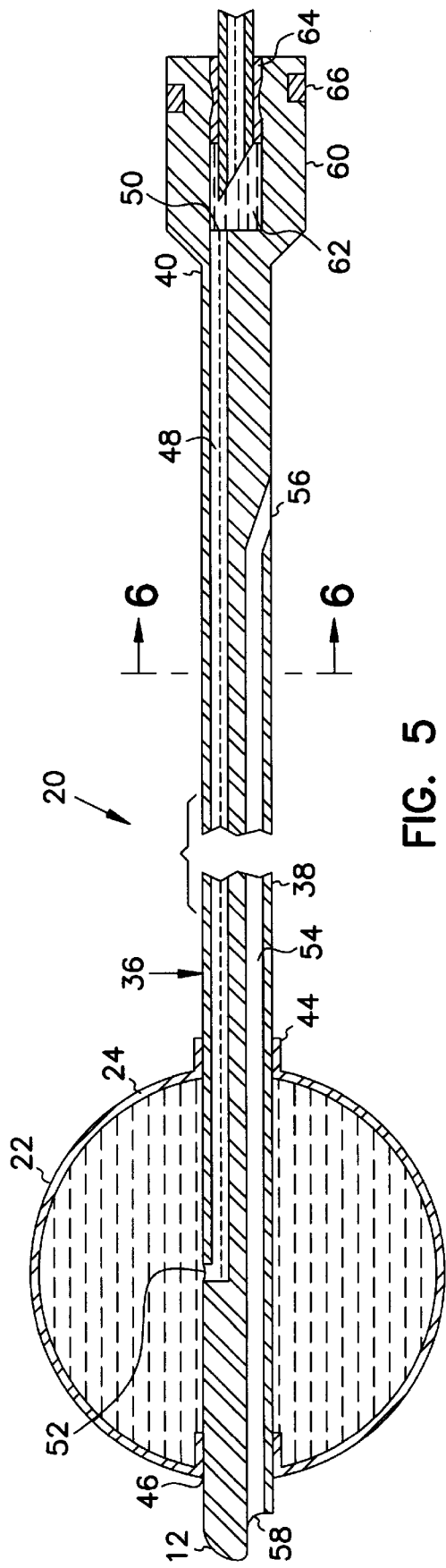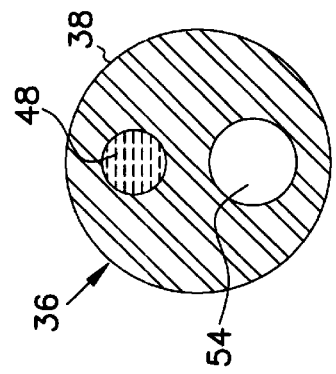
FIG. 5
FIG. 6

ADJUSTABLE IMPLANTABLE GENITOURINARY DEVICE

RELATED U.S. APPLICATION

This patent application is a continuation-in-part of U.S. patent application Ser. No. 08/873,444 filed Jun. 12, 1997.

FIELD OF THE INVENTION

The invention relates generally to implantable medical devices and in particular to implantable medical devices for treating urinary incontinence.

BACKGROUND OF THE INVENTION

Various implantable devices, such as distensible medical devices, are known in which the distensible medical devices are implanted into the tissue of a human to treat urinary incontinence. These devices have typically relied upon restricting or constricting the urethra of the patient to maintain continence.

U.S. Pat. No. 4,733,393 to Haber et al. is an attempt at such a proposed device. U.S. Pat. No. 4,733,393 relates to a hypodermically implantable genitourinary prosthesis which provides an extensible, inflatable tissue expanding membrane to be located in proximal urethral tissue to add bulk to these tissues for overcoming urinary incontinence by localized increase in tissue volume.

U.S. Pat. No. 4,802,479 to Haber et al. is an attempt at an instrument for dispensing and delivering material to an inflatable membrane of a genitourinary prosthesis within the tissues of a patient for overcoming urinary incontinence. U.S. Pat. No. 4,832,680 to Haber et al. relates to an apparatus for hypodermically implanting a genitourinary prosthesis comprising an extensible containment membrane for retaining a fluid or particulate matter which is injected from an external source.

U.S. Pat. No. 5,304,123 to Atala et al. relates to a detachable membrane catheter incorporated into an endoscopic instrument for implantation into the suburethral region of a patient. Also, U.S. Pat. No. 5,411,475 to Atala et al. discusses a directly visualized method for deploying a detachable membrane at a target site in vivo.

Once inflated, these devices maintain pressure on the urethra of the patient in an attempt to assist with continence. However, these devices are prone to being under or over inflated at time of implant, leading to undesirable postoperative results. For example, if the devices are overinflated it may cause the urethra to be restricted too tightly, and the patient is at risk for retention, a condition where the patient cannot pass urine. Such a condition could lead to kidney damage, necessitating major corrective surgery or at minimum use of self-catheterization to empty the bladder on a regular basis thus increasing the risk of urinary tract infection.

Furthermore, once these devices have been implanted within the patient, the only means of removing them in the event of a postoperative problem or device malfunction is through major surgery. Also, the devices are secured within the tissues of the patient, so there is the possibility of the devices migrating back along the pathway created in inserting them, a problem which has been noted with prior art devices. Thus, an important medical need exists for an improved implantable device for treating urinary incontinence.

SUMMARY OF THE INVENTION

The present invention provides an implantable device and a method for its use in restricting a body lumen. In one embodiment, the body lumen is a urethra, where the implantable device is used to coapt the urethra to assist the patient in urinary continence. The implantable medical device has the advantage of being adjustable both at the time of implantation and postoperatively. This postoperative adjustability of the implantable medical device allows a physician to regulate the amount of pressure applied to the urethra to ensure continence of the patient and to minimize iatrogenic effects.

In one embodiment of the invention, a patient's incontinence is treated by positioning one or more of the implantable devices adjacent to at least one side of a patient's urethra so as to adjust liquid flow resistance in the urethra. This is accomplished by using the implantable devices to coapt the patient's urethra so as to maintain a transverse cleft or slit structure of the collapsed urethra and thereby provide sufficient flow resistance to ensure continence, while still allowing the patient to consciously discharge urine when necessary.

The device according to one embodiment of the invention is intended to work immediately adjacent to the urethral wall of a patient to create an increase in urethral coaptation and flow resistance. However, in the prior art devices any tissue change which may occur postoperatively such as a reduction in tissue edema associated with the procedure may cause a reduction in clinical effect because of the reduced coaptation and resistance after the swelling has subsided. Although some minor degree of adjustability is available at the time of implantation in the prior art devices, not until the availability of the present invention is it possible to access the implanted device and adjust the membrane volume after implantation in a postoperative manner.

In one embodiment, the implantable device for treating urinary incontinence comprises an adjustable element having a continuous wall or membrane, where the wall includes an inner surface defining a chamber. The continuous wall is constructed of at least one material that is substantially self-sealing, and therefore, is able to withstand multiple punctures, for example from non-coring hypodermic needles, during postoperative adjustments of the adjustable element.

In one embodiment, the continuous wall is constructed of a biocompatible resiliently elastomeric polymer or polymer blend of polyurethane, silicone, or the like. In an additional embodiment, the continuous wall of the adjustable element has an outer surface generally defining a sphere. In yet another embodiment, the continuous wall has an outer surface generally defining an elongate body having semi-spherical end portions.

During the postoperative adjustments, the adjustable element is expanded or contracted (i.e., the volume of the adjustable element is increased or decreased) due to fluid volume introduced into the chamber. In one embodiment, fluid volume is introduced into the chamber through a hollow non-coring needle, such as a hypodermic needle, inserted through the wall of the adjustable element. The self-sealing ability of the wall allows for such adjustments by needles during one or more postoperative occasions without compromising the pressure retaining ability of the wall of the adjustable element.

In an additional embodiment, the implantable device includes one or more reinforcing structures positioned between the inner surface and an outer surface of the continuous wall. In one embodiment, woven or layered fibers of polyester, nylon, polypropylene, polytetrafluoroethylene (such as TEFLON) or other polymers having a high durometer measure or high modulus constitute the reinforcing structures. The reinforcing structures help to maintain structural integrity and the shape of the adjustable element during the initial inflation and any postoperative adjustments made thereafter.

In an additional embodiment, the continuous wall of the adjustable element has a porous polymer structure that allows the movement of water between the outer surface and the inner surface. A hydrophilic polymer is substantially encapsulated in the chamber, where the hydrophilic polymer absorbs water to expand the implantable device. Once implanted within a patient, the volume of the adjustable element is altered (i.e., expanded or contracted) during implantation and/or postoperatively by introducing or removing the hydrophilic polymer from the chamber. In one embodiment, the hydrophilic polymer is hyaluronic acid, polyvinylpyrrolidone, polyethylene glycol, or carboxy methyl cellulose.

In an additional embodiment, the implantable medical device includes a tubular elongate body connected to and sealed to the adjustable element. The tubular elongate body includes a first interior passageway extending longitudinally in the tubular elongate body from a first port at the proximal end to a second port in fluid communication with the chamber of the implantable device for adjustably expanding or contracting the expandable element by applied fluid volume introduced through the first port.

The tubular elongate body further includes a second interior passageway extending longitudinally in the tubular elongate body from a proximal opening through the peripheral surface positioned between the proximal and the distal end to a distal opening through the distal end of the tubular elongate body. This second interior passageway is of sufficient diameter to receive and guide an obturator for the insertion of the implantable device into a human body.

This embodiment of the implantable device also includes a rear port element coupled to the proximal end of the tubular elongate body. The rear port element including a cavity in fluid communication with the first port of the first interior passageway. An elastic septum is included on the rear port element, and is retained in the rear port element by a clap ring located around the rear port element.

An important improvement provided by one embodiment of the present invention resides in the ability to access the implanted rear port element located close to the surface of the patient's skin to adjustably restrict the urethra. This is accomplished by controlling the volume of a fluid, such as a flowable material, in the adjustable element after it has been implanted in the patient. Suitable flowable materials for introduction into the expandable membrane include a saline liquid, a flowable gel, or a slurry of small particles such as silicone in a fluid carrier. Moreover, the flowable material may be made radiopaque to facilitate fluoroscopic visualization for postoperative inspection.

The post implantation, or postoperative, urethral restriction is realized by the adjustable element acting on tissue adjacent to the walls of the urethral lumen and forcefully closing the urethral lumen. Voiding of urine from the bladder only occurs when the intravesicular pressure overcomes the resistance established by the adjustable element.

An important feature of the implantable device of the present invention relates to the adjustable element or membrane which is accessible for subsequent adjustment in volume through the rear port element located under a patient's skin, remotely from the adjustable element. Another important feature of the present invention over the prior art devices is the convenient in vivo postoperative adjustability of both pressure and size of the adjustable element.

BRIEF DESCRIPTION OF THE DRAWINGS

In the drawings, where like numerals describe like components throughout the several views:

FIG. 5 is a longitudinal cross-sectional view of the implantable device of FIG. 4;

FIG. 6 is a cross-sectional view taken along line 6—6 of FIG. 5;

DETAILED DESCRIPTION OF THE INVENTION

Figure 1A:
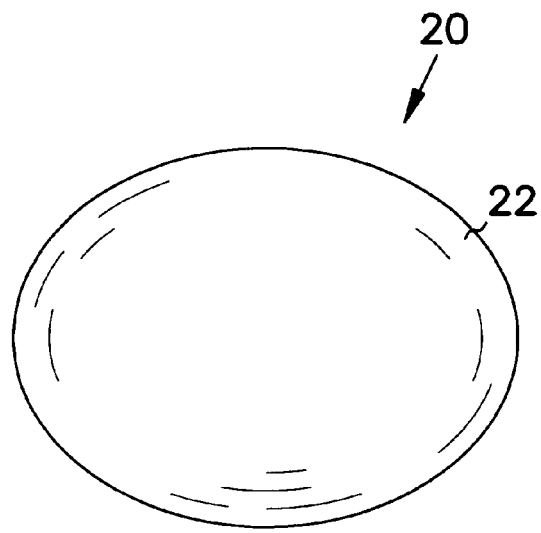
FIGS. 1(A–D) is a schematic view of an adjustable element according to one embodiment of the present invention.

In the following detailed description, reference is made to the accompanying drawings which form a part hereof and in which is shown by way of illustration specific embodiments in which the invention may be practiced. These embodiments are described in sufficient detail to enable those skilled in the art to practice and use the invention, and it is to be understood that other embodiments may be utilized and that logical, and structural changes may be made without departing from the spirit and scope of the present invention. The following detailed description is, therefore, not to be taken in a limiting sense and the scope of the present invention is defined by the appended claims and their equivalents.

In FIGS. 1(A–D) and 2 of the drawings, there is shown an implantable device 20 for restricting a body lumen. In one embodiment, the implantable device 20 is for treating ureteral reflux of a patient by implanting at least one of the implantable devices adjacent one or both ureter proper. In an alternative embodiment, the implantable device 20 is for treating urinary incontinence by implanting at least one of the implantable devices adjacent the urethra.

Implantable devices designed for treating urinary incontinence are typically referred to as a genitourinary prosthesis. Many designs for genitourinary prosthesis have been proposed. In one such proposed embodiment, genitourinary prosthesis are comprised of elastomeric, elliptoidally or spherically-shaped containment membranes which have an interior chamber designed to receive a measured supply of fluid to inflate the prosthesis. One such description of a genitourinary prosthesis is also provided in a co-pending U.S. patent application Ser. No. 08/873,444, entitled "Implantable Device and Method for Adjustably Restricting a Body Lumen" filed Jun. 12, 1997, by Burton et al., which is hereby incorporated by reference in its entirety.

In treating urinary incontinence, the prosthesis are delivered within the body to a location that is typically within the periurethral tissue and adjacent to the urethra to enable a patient to overcome urinary incontinence by means of increasing both localized tissue volume and passive occlusive pressure upon the urethral mucosa.

The prosthesis is typically mounted on a hollow noncoring needle, such as a hypodermic needle, which is releasably connected to a fluid source, such as a syringe element. In order to facilitate inserting the prosthesis into position, the prosthesis is housed within a tubular body, such as a trocar tube, where the tubular body is designed to penetrate the tissues of the patient, thus allowing the proper placement of the prothesis. Alternatively, the prosthesis could be mounted at or on a distal end of a trocar tube to allow for delivery of the prosthesis within the patient.

Once the prosthesis has been positioned within the body, it is inflated by infusing a measured supply of fluid volume, including fluid volume having particulate matter into the interior of the of the membrane of the prosthesis. Fluids suitable for infusing into the prothesis include, but are not limited to, sterile saline solutions, polymer gels such as silicone gels or hydrogels of polyvinylpyrrolidone, polyethylene glycol, or carboxy methyl cellulose for example, high viscosity liquids such as hyaluronic acid, dextran, polyacrylic acid, or polyvinyl alcohol for example, or liquids that coagulate on contact with body fluids. The fluids also include fluids having a variety of particulate matter, and include, but are not limited to particles have a spherical shape, an elongate shape, or particles having a cross sectional star shape. Once the prothesis has been inflated, the needle is withdrawn from the prosthesis and the tubular body is withdrawn from the body, leaving the inflated prothesis in position.

Figure 2:
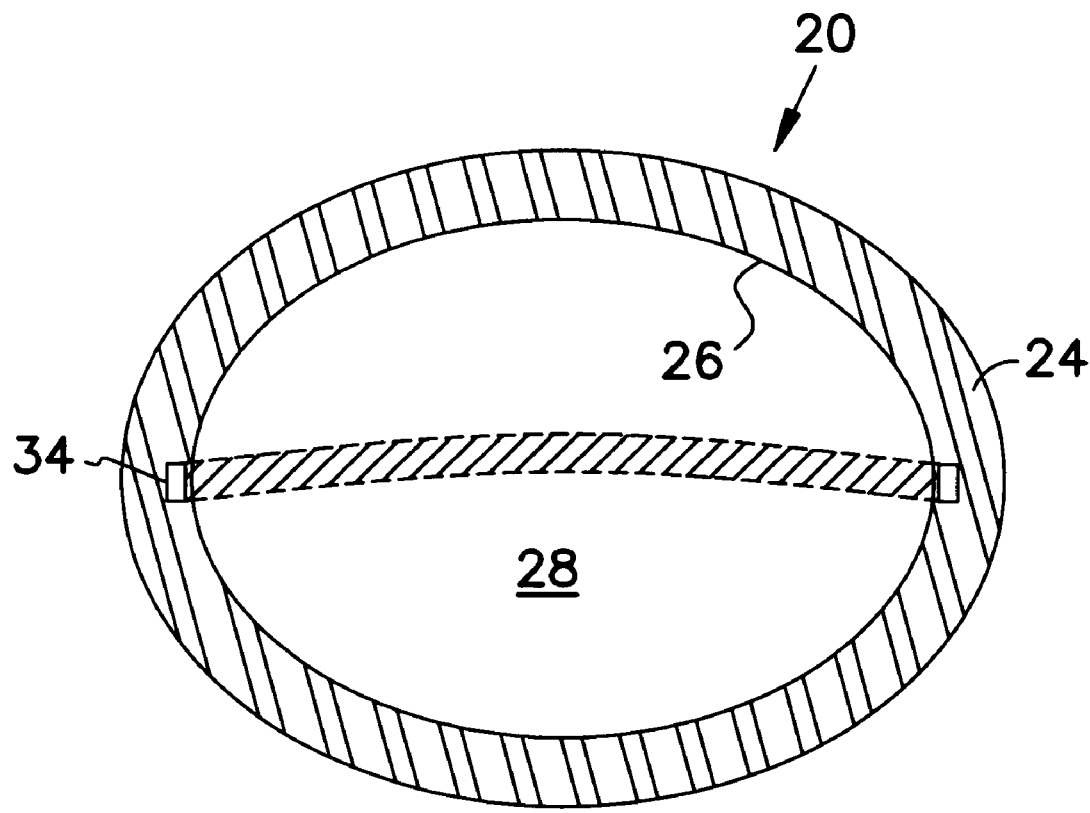
FIG. 2 is a schematic cross-sectional view of the adjustable element of FIG. 1.

FIGS. 1A and 2 shows one embodiment of an implantable device 20 for restricting a body lumen comprising an adjustable, self-sealing element 22 having a continuous wall 24. The continuous wall 24 includes an inner surface 26 defining a chamber 28. Furthermore, the continuous wall 24 is constructed of at least one material that is substantially self-sealing to allow for the adjustable element 22 to be expanded or contracted due to fluid volume introduced into the chamber 28. In one embodiment, the continuous wall 24 itself is constructed of a self-sealing material. In an alternative embodiment, the inner surface 26 of the adjustable element 22 has a material that imparts a self-sealing ability to the adjustable element 22 such as crosslinked silicone gel, polyvinylpyrrolidone, or karaya gum for example.

Figure 1B:
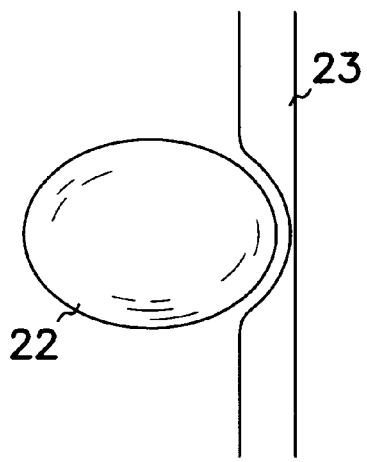
Figure 1C:
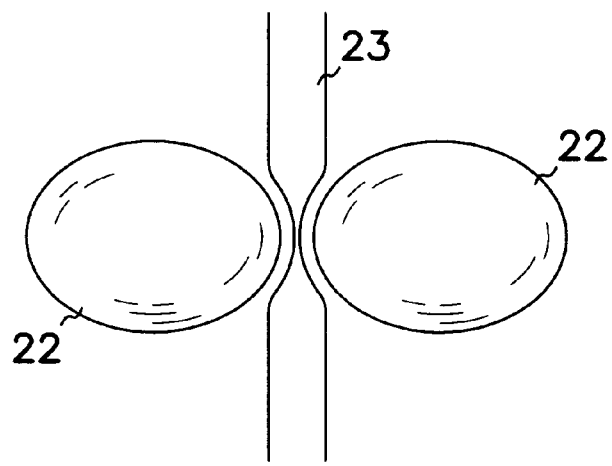
Figure 1D:
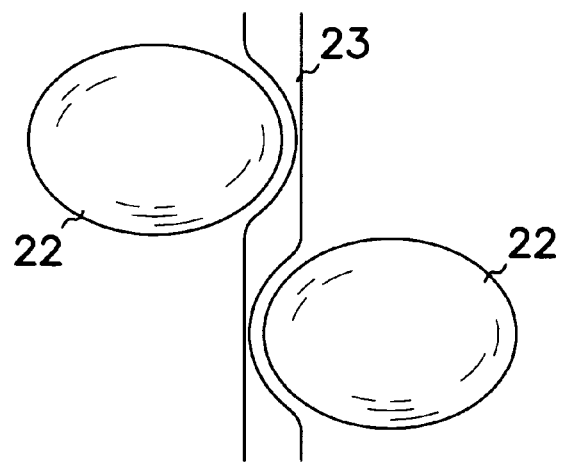

FIGS. 1B–D show several embodiments of genitourinary prosthesis implanted in a patient. FIG.1B is one embodiment of positioning the adjustable element 22 of the present invention, where one adjustable element 22 is positioned adjacent a urethra 23 of the patient. In an alternative embodiment, FIG. 1C shows two of the adjustable element 22 positioned adjacent the urethra 23, where each of the adjustable element 22 are generally disposed on opposite sides of and in a similar plane perpendicular to the urethra 23. In an additional embodiment, FIG. 1D shows two of the adjustable element 22 positioned adjacent the urethra 23, where each of the adjustable element 22 are generally disposed on opposite sides of the urethra 23, with each of the adjustable elements 22 in generally a different plane perpendicular the urethra 23 to create at least two portions of the urethra having a coapted portion and leading to the urethra 23 having a tortious configuration. In an alternative embodiment, the adjustable element 22 is placed next to a ureter proper.

In one embodiment, the continuous wall 24 is intended and designed to be pierced by hollow non-coring needles on one or more occasions for adjusting the volume of the adjustable element during both the implanting of the adjustable element and during subsequent postoperative adjustment of the adjustable element. As such, the continuous wall 24 is constructed of a material that is tear-resistant and biocompatible. In one embodiment, the material is also substantially self-sealing during and after being pierced by a hollow non-coring needle to maintain fluid volume within the chamber 28 of the adjustable element.

In an additional embodiment, the adjustable element 22 has two or more continuous walls 24, where the continuous walls 24 are arranged concentrically with one of two or more continuous walls 24 being within another continuous wall 24 (not shown). The two or more continuous walls 24 of the present embodiment are separated from each other due to the presence of fluid between the continuous walls 24. In one embodiment, the chambers created by each of the continuous walls 24 are filled with any combination of fluids described within this detailed description.

In one embodiment, the continuous wall is constructed of a biocompatible resiliently elastomeric polymer or polymer blend of polyurethane, silicone, or the like. In this embodiment, the continuous walls 24 stretch as the adjustable element 22 expands or contracts to a desired size. In an alternative embodiment, the continuous wall is constructed of a biocompatible non-resilient polymer or polymer blend of polyethylene, polytetraflouroethylene, polystyrene, or polyesteretherketone (PEEK). In this embodiment, the continuous wall 22 of the adjustable element 22 expand to a predetermined shape. The adjustable element is formed into a variety of shapes. In one embodiment, the outer surface 32 of the continuous wall 24 generally defines a spherical shape. In an alternative embodiment, the outer surface 32 of the continuous wall 24 generally defines an elongate body having semi-spherical end portions. In one embodiment, a adjustable element 22 being constructed of a biocompatible resiliently elastomeric polymer or polymer blend typically retains the same general cross-sectional shape deflated as when inflated. In an alternative embodiment, when the adjustable element 22 is constructed of a biocompatible non-resilient elastomeric polymer or polymer blend the deflated adjustable element 22 typically has a configuration in which the continuous wall 24 has a folded structure which as the adjustable element 22 is inflated changes to take on a preformed cross-sectional shape and size and/or diameter.

Figure 3:
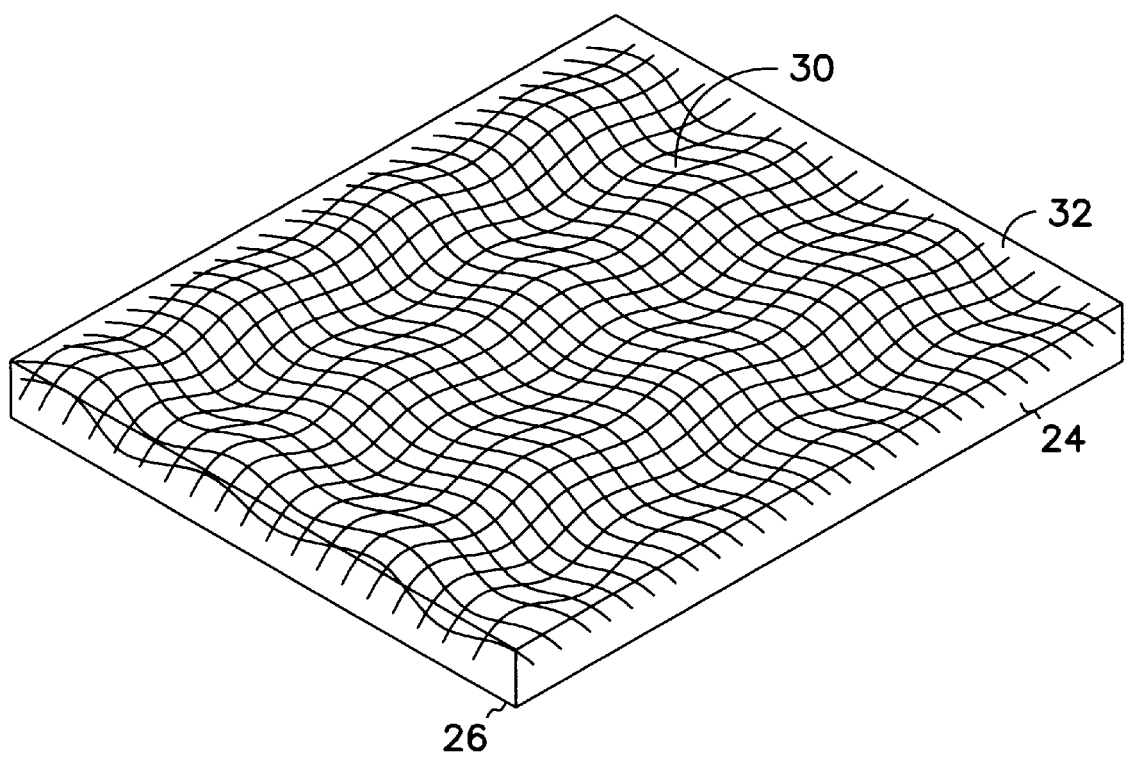
FIG. 3 is one embodiment of reinforcing structures within the continuous wall of the adjustable element.

Referring now to FIG. 3, there is shown an embodiment of a portion of the continuous wall 24, where the continuous wall 24 further includes one or more reinforcing structures 30 positioned between the inner surface 26 and an outer surface 32 of the continuous wall 24. In one embodiment, the one or more reinforcing structures 30 are designed to support the structural integrity of the continuous wall 24, helping to provide the substantially self-sealing nature of the adjustable element 22, and to assist in retaining particles within the chamber 28 of the adjustable element 22. In one embodiment, the one or more reinforcing structures 30 are fibers constructed from the group comprising one or more of polyester, nylon, polypropylene, polytetrafluoroethylene (such as TEFLON) or other polymers having a high durometer measure or high modulus constitute the reinforcing structures.

In one embodiment, the fibers of the one or more reinforcing structures 30 are woven into a support structure that is positioned between the inner surface 26 and the outer surface 32 of the continuous wall 24. In an additional embodiment, the fibers of the one or more reinforcing structures 30 are less elastic than the continuous wall 24, and the woven support structure has a lose weave configuration to allow for the support structure to expand or contract with the expansion and contraction of the continuous wall 24 of the adjustable element 22.

In an alternative embodiment, the fibers of the one or more reinforcing structures 30 are substantially non-elastic and are arranged in a woven configuration, where the fibers have a kinked structure that allows them to expand or contract with the expansion and contraction of the continuous wall 24 of the adjustable element 22.

The one or more reinforcing structures 30 provide the adjustable element 22 with reinforced structural integrity and an increased ability to retain infused particles within the chamber 28 of the adjustable element 22. In one embodiment, the fibers of the one or more reinforcing structures 30 woven into the support structure provide a "rip-stop" function. As an example, the woven support structure allows for rip-stop protection from tears in the continuous wall 24 due to insertion and removal of hollow non-coring needles through the continuous wall 24. In an additional embodiment, the woven support structure prevents the migration of particle from the chamber 28, where the particles are used to inflate the adjustable element 22. In one embodiment, the particles are prevented from migrating out of the chamber 28 due to the tightness of the weave of the support structure.

As previously mentioned, a variety of particulate matter is suitable for infusing into the chamber 28 of the adjustable element 22. The particulate matter is typically suspended in a carrier fluid, or lubricious fluid, however, this is not necessary. Examples of particulate matter shapes include collapsible hollow spheres or those having multiple projecting arms or structures from a central axis. In one embodiment, the structure of the particulate matter has a larger diameter than both the inner diameter of the hollow non-coring needle and the opening in the woven structure of the reinforcing structure 30. To inject the particulate matter into the chamber 28 of the adjustable element 22, the surface of the particulate matter is physically distorted to allow it to pass through the inner diameter of the hollow non-coring needle, such as the hollow spheres collapsing or the projecting arms bending. Once the particulate matter has passed through the hollow non-coring needle, the particulate matter expands back to a size greater than the hole created by the needle, thus making the device self sealing.

In an alternative embodiment, the particulate matter is an elongate body, such as a tubular elongate structure, such that the particulate matter can pass longitudinally through the hollow non-coring needle, but once inside the adjustable element 22 their random orientation would essentially prevent them from passing back through any needle hole created by the hollow non-coring needle.

In an alternative embodiment, the inner diameter of the hollow non-coring needle is sufficient to pass the particulate matter, however the structure of the particulate matter has a larger diameter than the openings in the woven structure of the reinforcing structure 30. In this embodiment, inserting the hollow non-coring needle distorts the mesh of the woven structure of the reinforcing structure 30 to allow the hollow non-coring needle to pass through the continuous wall 24 and into the chamber 28.

Alternatively, the particle is made of a hydrophillic material such as polyvinylpyrrolidone, polyethylene glycol, carboxy methyl cellulose, hyaluronic acid, or the like, which expands once inside the adjustable element 22 due to the absorption of liquid that is either delivered with the particles or passes through at least a portion of the continuous wall 24 of the adjustable element 22.

In an additional embodiment, a detectable marker 34 is imbedded in the continuous wall 24 of the adjustable element 22. The detectable marker 34 allows the adjustable element 22 to be located and its shape to be visualized within the tissues of a patient using any number of visualization techniques which employ electromagnetic energy as a means of locating objects within the body. In one embodiment, the detectable marker is constructed of tantalum and the visualization techniques used to visualize the adjustable element 22 are x-ray or fluoroscopy as are known in the art. In an additional embodiment, the one or more reinforcing structures 30 are labeled with tantalum to allow the adjustable element 22 to be visualized using x-ray, fluoroscopy or other visualization techniques as are known in the art.

Figure 4:
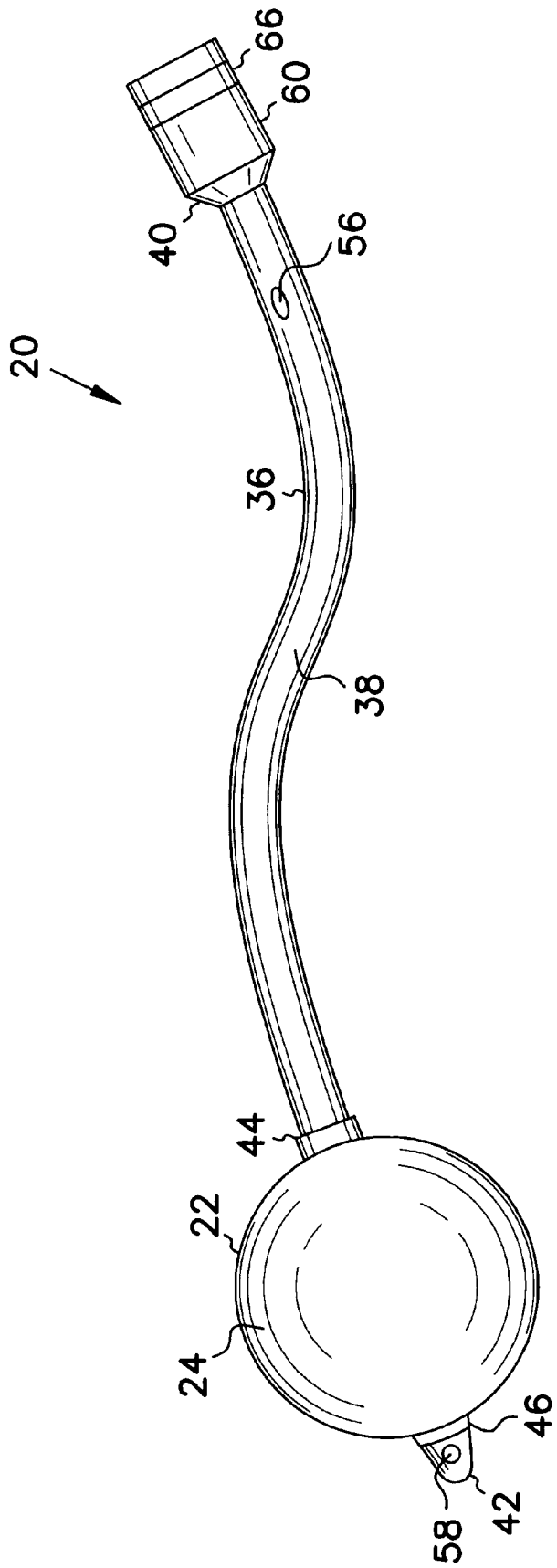
FIG. 4 is one embodiment of an implantable device according to the present invention.

Referring now to FIGS. 4, 5, and 6 there is shown an alternative embodiment of the implantable device 20 further includes a tubular elongate body 36, where the tubular elongate body 36 has a peripheral surface 38, a proximal end 40 and a distal end 42. The adjustable element 22 has at least one opening through the continuous wall 24 to which the peripheral surface 38 is connected to and sealed to the adjustable element 22. The tubular elongate body 36 is inserted through the first opening 44 and the second opening 46 such that the distal end 42 of the elongate body 36 partially extends beyond the outer surface 32 of the adjustable element 22. The peripheral surface 38 is then sealed to the walls creating the first opening 44 and the second opening 46. In one embodiment, the peripheral surface 38 is sealed to the openings using a chemical or polymer adhesive, such as silicone. In an alternative embodiment, the peripheral surface 38 is sealed to the openings using sonic welding techniques as are known in the art.

The tubular elongate body 36 further includes a first interior passageway 48 extending longitudinally in the tubular elongate body 36 from a first port 50 at the proximal end 40 to a second port 52 in fluid communication with the chamber 28 of the implantable device for adjustably expanding or contracting the expandable element 22 by applied fluid volume introduced through the first port 50.

In an additional embodiment, the tubular elongate body 36 further includes a second interior passageway 54 extending longitudinally in the tubular elongate body 36 from a proximal opening 56 through the peripheral surface 38 positioned between the proximal end 40 and the distal end 42 to a distal opening 58 through the distal end 42 of the tubular elongate body 36. In one embodiment, the second interior passageway 54 is of sufficient diameter to receive and guide an obturator for the insertion of the implantable device 20 into a human body. In an alternative embodiment, the obturator is removably attached at the distal end 42 and passes outside the expandable element 22 and along side the elongate body 36 to allow placement of the device without the need for the second interior passageway 54.

The implantable device 20 further includes a rear port element 60 coupled to the proximal end 40 of the tubular elongate body 36. In one embodiment, the rear port element 60 is coupled to the proximal end 40 of the elongate body 36 using chemical adhesives, or alternatively, using sonic welding techniques as are known in the art. In an additional embodiment, the rear port element 60 and proximal end 40 are formed together in an polymer extrusion process or polymer casting process as are known in the art.

The rear port element 60 includes a cavity 62, where the cavity 62 is in fluid communication with the first port 50 of the elongate body 36. The rear port element 60 also includes an elastic septum 64 through which the cavity 62 is accessed. The elastic septum 64 is retained in the rear port element 60 by a clamp ring 66 located around the rear port element 60. In one embodiment, the clamp ring 66 is made of a biocompatible material, such as, for example, titanium. In one embodiment, the elastic septum 64 is made of a biocompatible material, such as, for example, silicone or polyurethane.

Figure 7:
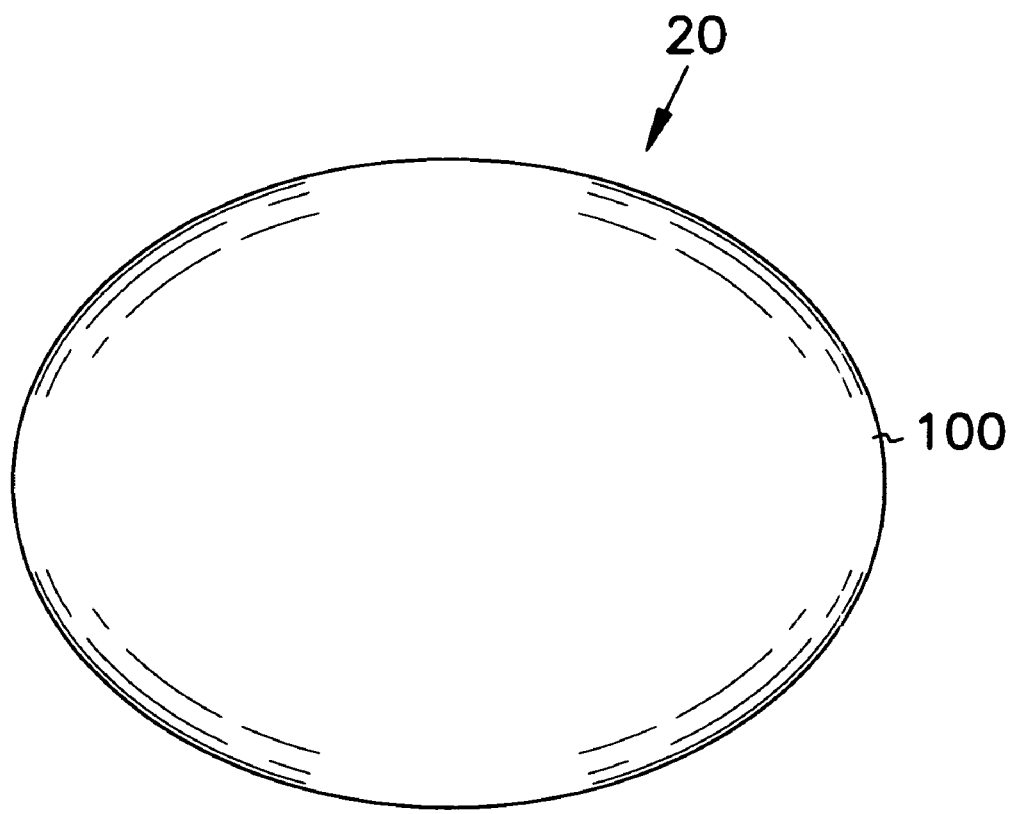
FIG. 7 is a schematic view of an adjustable element according to one embodiment of the present invention.
Figure 8:
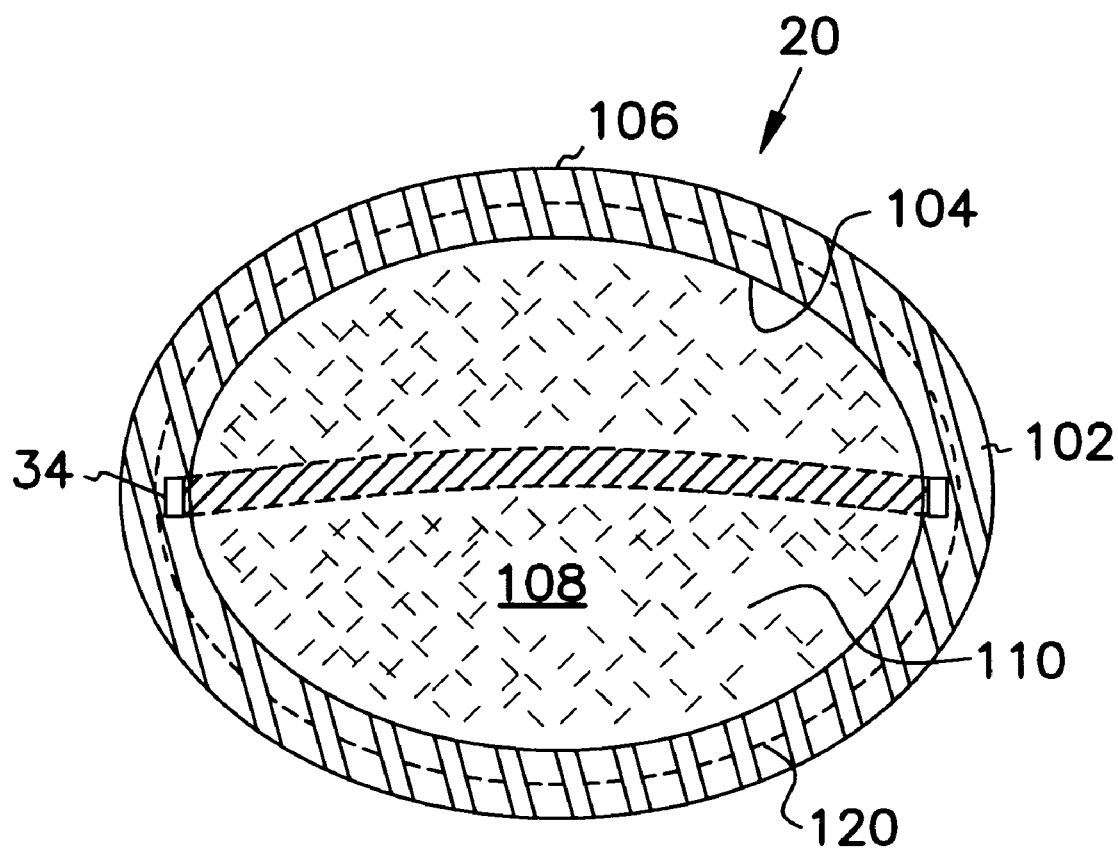
FIG. 8 is a schematic cross-sectional view of the adjustable element of FIG. 7.

Referring now to FIGS. 7 and 8, there is shown an alternative embodiment of the implantable device 20 for treating urinary incontinence or ureteral reflux. The implantable device 20 comprises an adjustable element 100 having a continuous wall 102, including an inner surface 104 and an outer surface 106, where the inner surface 104 defines a chamber 108. The continuous wall 102 also has at least a portion of the continuous wall that is constructed of a porous polymer structure that allows the movement of water between the outer surface 106 and the inner surface 104. A hydrophilic polymer 110 is substantially encapsulated in the chamber 108, where the hydrophilic polymer 110 absorbs water. As the hydrophilic polymer 110 absorbs water, it causes the chamber 108 to expand, thus enlarging the adjustable element 100.

In one embodiment, the continuous wall 102 is intended and designed to be pierced by hollow non-coring needles on one or more occasions for adjusting the volume of the adjustable element during both the implanting of the adjustable element and during subsequent postoperative adjustment of the adjustable element. As such, the continuous wall 102 is constructed of a material that is substantially self-sealing during and after being pierced by a hollow non-coring needle to maintain fluid volume within the chamber 108 of the adjustable element, and the adjustable element expands or contracts by introducing or removing the hydrophilic polymer from the chamber.

Referring now to FIG. 8, there is shown an embodiment of a portion of the continuous wall 102, where the continuous wall 102 further includes one or more reinforcing structures 120 positioned between the inner surface 104 and the outer surface 106 of the continuous wall 102. In one embodiment, the one or more reinforcing structures 120 are fibers constructed from the group comprising one or more of polyester, nylon, polypropylene, polytetrafluoroethylene (such as TEFLON) or other polymers having a high durometer measure or high modulus constitute the reinforcing structures.

In one embodiment, the fibers of the one or more reinforcing structures 120 are woven into a support structure that is positioned between the inner surface 104 and the outer surface 106 of the continuous wall 102. In an additional embodiment, the fibers of the one or more reinforcing structures 120 are less elastic than the continuous wall 102. The woven support structure, in one embodiment, has a lose weave configuration to allow for the support structure to expand or contract with the expansion and contraction of the continuous wall 102 of the adjustable element 100.

In an alternative embodiment, the fibers of the one or more reinforcing structures 120 are substantially non-elastic and are arranged in a woven configuration, where the fibers have a kinked structure that allows them to expand or contract with the expansion and contraction of the continuous wall 102 of the adjustable element 100.

The one or more reinforcing structures 120 provide the adjustable element 100 with reinforced structural integrity and an increased ability to retain particles within the chamber 108 of the adjustable element 100. In one embodiment, the fibers of the one or more reinforcing structures 120 woven into the support structure provide a "rip-stop" function. As an example, the woven support structure allows for rip-stop protection from tears in the continuous wall 102 due to insertion and removal of hollow non-coring needles through the continuous wall 102. In an additional embodiment, the woven support structure prevents the migration of particle from the chamber 108, where the particles are used to inflate the adjustable element 100. In one embodiment, the particles are prevented from migrating out of the chamber 108 due to the tightness of the weave of the support structure.

In an additional embodiment, a detectable marker 122 is imbedded in the continuous wall 102 of the adjustable element 100. The detectable marker 122 allows the adjustable element 100 to be located and its shape to be visualized within the tissues of a patient using any number of visualization techniques which employ electromagnetic energy as a means of locating objects within the body. In one embodiment, the detectable marker is constructed of tantalum and the visualization techniques used to visualize the adjustable element 100 are x-ray or fluoroscopy as are known in the art. In an additional embodiment, the one or more reinforcing structures 120 are labeled with tantalum to allow the adjustable element 100 to be visualized using x-ray, fluoroscopy or other visualization techniques as are known in the art.

The hydrophilic material used within the chamber 108 of the adjustable element 100 is selected from a group comprising one or more of polyvinylpyrrolidone, polyethylene glycol, carboxy methyl cellulose, or hyaluronic acid. In one embodiment, the hydrophilic polymer have a particulate structure, where the hydrophilic polymer takes the form of discrete, individual polymeric units. Additionally, the particulate structure of the hydrophilic polymer has an average diameter that is greater than an average diameter of pores of the porous polymer structure. In an additional embodiment, the porous polymer structure of the continuous wall 102 has openings that are less than or equal to 200 micrometers.

In one embodiment, the continuous wall 102 is constructed of a biocompatible resiliently elastomeric polymer or polymer blend of polyurethane, silicone, or the like. In this embodiment, the continuous wall 102 stretches as the adjustable element 100 expands or contracts to a desired size. In an alternative embodiment, the continuous wall 102 is constructed of a biocompatible non-resilient polymer or polymer blend of polyethylene, polyesterterethalate, or high modulus polystyrene, or polyesteretherketone. In this embodiment, the continuous wall 102 of the adjustable element 100 expand to a predetermined shape. The adjustable element 100 is formed into a variety of shapes. In one embodiment, the outer surface 106 of the continuous wall 102 generally defines a spherical shape. In an alternative embodiment, the outer surface 106 of the continuous wall 102 generally defines an elongate body having semispherical end portions. In one embodiment, a adjustable element 102 being constructed of a biocompatible resiliently elastomeric polymer or polymer blend typically retains the same general cross-sectional shape deflated as when inflated. In an alternative embodiment, when the adjustable element 102 is constructed of a biocompatible non-resilient elastomeric polymer or polymer blend the deflated adjustable element 102 typically has a configuration in which the continuous wall 102 has a folded structure which as the adjustable element 100 is inflated changes to take on a preformed cross-sectional shape and size and/or diameter.

Figure 9:
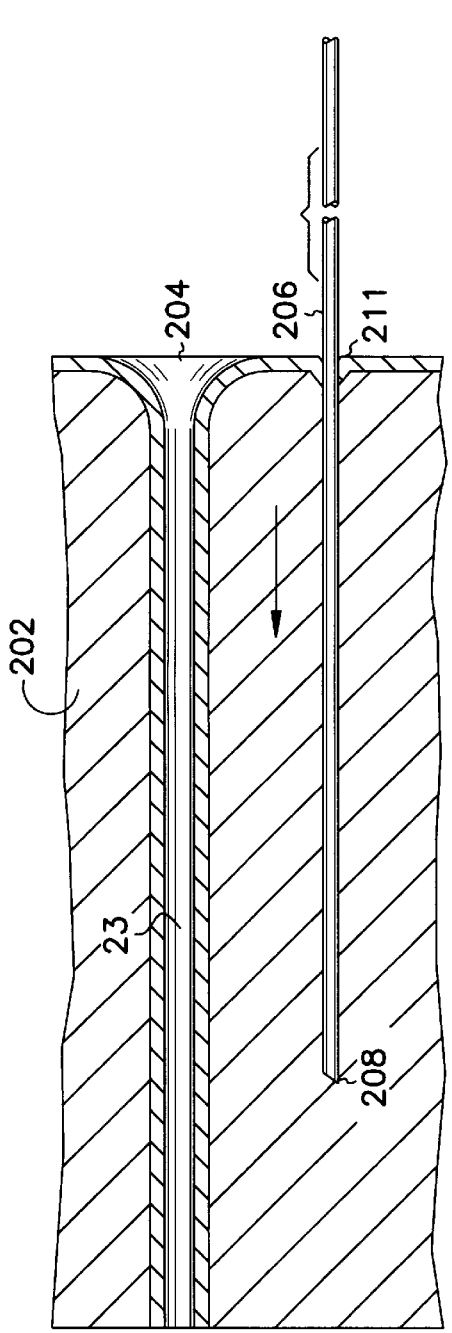
FIG. 9 is one embodiment of an obturator inserted into body tissue to an implant location adjacent a body lumen of a patient prior to insertion of the implantable device.
Figure 10:
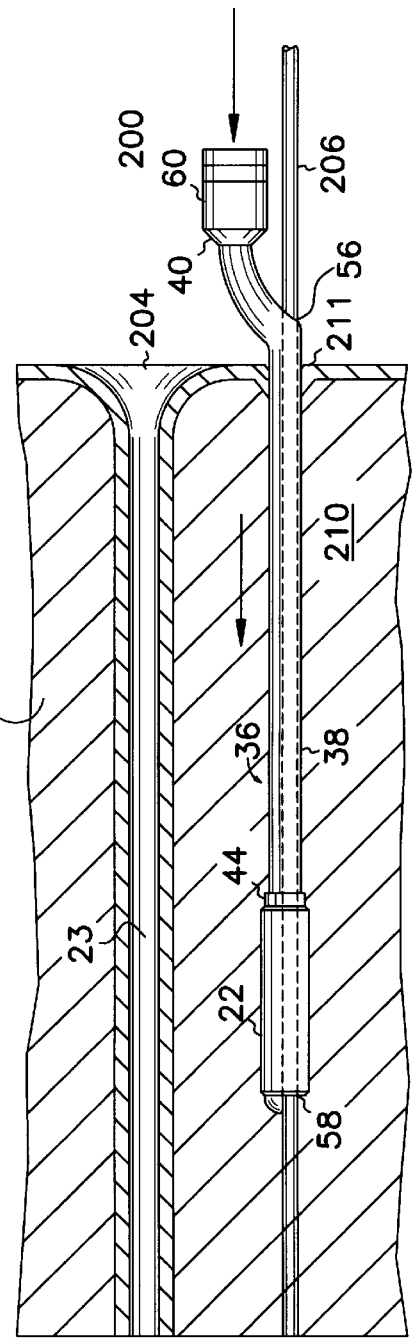
FIG. 10 is one embodiment of the implantable device placed over an obturator and partially advanced to the desired location with the adjustable element being deflated.

Referring now to FIGS. 9 and 10, there is shown an embodiment of the method of implanting one embodiment of the implantable device assembly 200 of the present invention for restricting a body lumen in a patient. The implantable device assembly 200 is adapted to be surgically implanted into body tissue 202 of a patient adjacent to a body lumen for coaptating the body lumen.

The implantable device assembly 200 comprises an obturator 206 having a cutting end 208 adapted for being inserted as a guide member into body tissue 202 to locate a portion of the obturator adjacent the body lumen to be restricted. Referring to FIG. 9, a physician after locating the body lumen, such as the urethra 23 of a patient, first makes a small incision in skin of the patient 211 and inserts the obturator 206 in the body tissue to a desired location adjacent the urethra 23. This procedure is usually carried out under a local anesthetic with visual guidance, for instance under fluoroscopy by the physician. The obturator 206 is of sufficient strength and rigidity to allow its insertion into the tissue 202 of the patient adjacent and parallel with the urethra 23.

Referring to FIG. 10, an implantable medical device 210, adapted for being surgically implanted into the tissue 202 adjacent to the body lumen, is then positioned onto the obturator 206 and advance into the tissue 202 of the patient. In one embodiment, the obturator 206 is inserted near the meatus urinarius 204 and advance through the periurethral tissue adjacent the urethra 23. In one embodiment, a detent or mark is provided on the obturator 206 which when aligned with a feature on the implantable medical device 210, such as a rear port element 60, ensures that an implantable medical device 210 is appropriately placed at the correct depth in the patient's body tissue. In an additional embodiment, the elongate body 36 of the implantable medical device 210 is available having a variety of lengths to accommodate the patient's physiological structure so as to facilitate placement of the elastic septum on the rear port element 60 near the patient's skin. Alternatively, the elongate body 36 effective length could be made adjustable by it having a helical shape similar to that of a coiled spring.

FIG. 10 shows one embodiment of the implantable medical device 210, where the implantable medical device 210 includes an adjustable element 22, a tubular elongate body 36, and a rear port element 60. The adjustable element 22 has a continuous wall, including an inner surface defining a chamber. The tubular elongate body 36, has a peripheral surface 38, a proximal end 40 and a distal end 44, where the peripheral surface is connected to and sealed to the adjustable element 22. The tubular elongate body includes a first interior passageway and a second interior passageway, the first interior passageway extending longitudinally in the tubular elongate body from a first port at the proximal end to a second port in fluid communication with the chamber of the implantable device for adjustably expanding or contracting the expandable element 22 by applied fluid volume introduced through the first port.

The second interior passageway also extends longitudinally in the tubular elongate body 36 from a proximal opening 56 through the peripheral surface 38 positioned between the proximal end 40 and the distal end 44 to a distal opening 58 through the distal end of the tubular elongate body 42. The second interior passageway being of sufficient diameter to receive and guide the obturator 206 for the insertion of the implantable device into the patient's body. The rear port element 60 of the implantable medical device 210 is coupled to the proximal end 40 of the tubular elongate body 36, where the rear port element includes a cavity in fluid communication with the first port of the first interior passageway.

In one embodiment, once the obturator 206 has been inserted into the patient's tissue, the portion of the obturator 206 extending from the patient's body is inserted into the distal opening 58 of the second interior passageway. The implantable medical device 210 is then advance or moved along or over the obturator 206 to position the adjustable element 22 adjacent the body lumen to be restricted and to position the rear port element subcutanesouly. In one embodiment, the adjustable element 22 is positioned adjacent a urethra. In an additional embodiment, two or more of the implantable medical devices 220 are implanted within the body tissue adjacent a urethra. The obturator 206 is then withdrawn from the tissue of the patient by pulling the obturator 206 through the proximal opening 56 of the second interior passageway, leaving the implantable medical device 210 in position.

Figure 11:
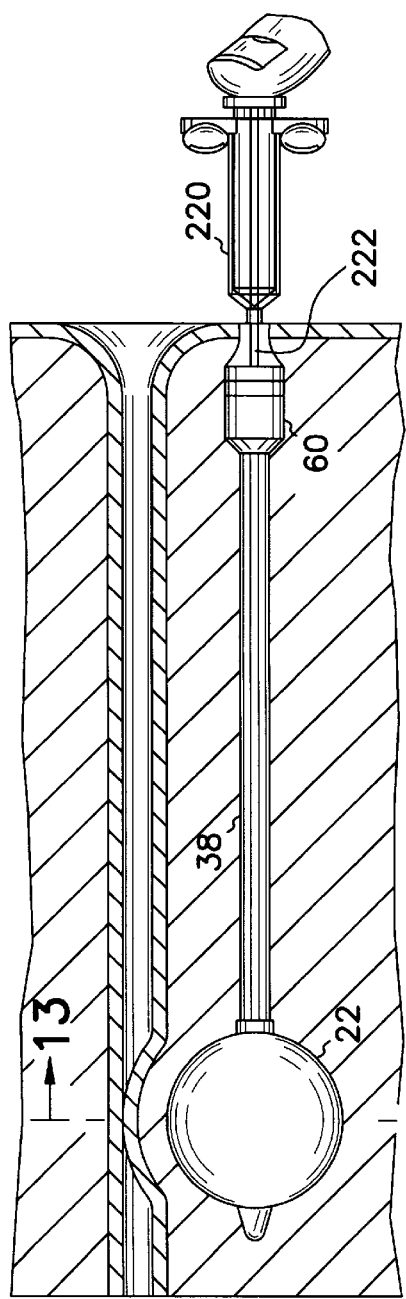
FIG. 11 is one embodiment of the implantable medical device implanted within the body tissue with the adjustable element expanded to cause the adjustable restriction of the body lumen.
Figure 13:
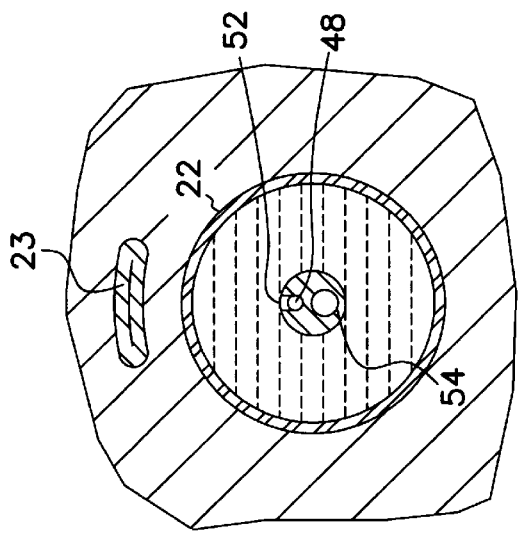
FIG. 13 is a cross-sectional view taken along line 13—13 of FIG. 11.
Figure 12:
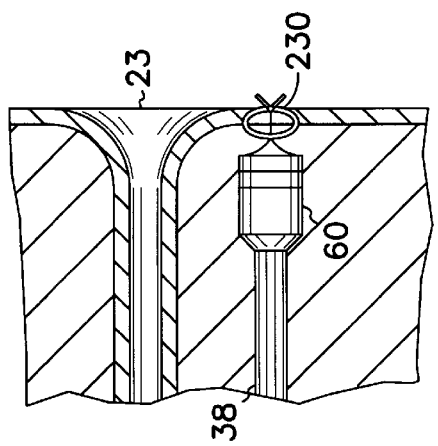
FIG. 12 is a partial view of one embodiment of the implantable medical device implanted within the body tissue.

Referring now to FIGS. 11, 12 and 13 there is shown one embodiment of the implantable medical device 210 implanted in the tissue of a patient for restricting a body lumen. In one embodiment, the body lumen is the urethra 23 and the implantable medical device 210 has been implanted in the periurethral tissue of the patient.

After the implantable medical device 210 has been advanced over the obturator 206 so that the contracted adjustable element 22 is in the desired position adjacent to the urethra 23, the urethra 23 is restricted to a desired degree by piercing the elastic septum with a needle of a syringe and injecting a flowable material through the first interior passageway into the adjustable element 22. The physician may determine the desired degree of restriction of urethra 23 by means such as infusing fluid through the urethra 23 past the restriction and measuring the back pressure. As illustrated by FIG. 11 the source of flowable material is usually a syringe 220 with a hollow non-coring needle 222 used to pierce the elastic septum, however alternate fluid containers with means for making a reversible connection to implantable medical device 210 could be used. The flowable material may be, for example, a saline solution, a flowable gel, or a slurry of particles in a liquid carrier. It may be advantageous to make the flowable material radiopaque so that the degree of membrane inflation may be viewed by x-ray.

An alternative method of delivery of the implantable medical device 210 could be to first withdraw obturator 206 from the body tissue and then inflate adjustable element 22.

A further alternative would be to first place the implantable medical device 210 over the obturator 206 outside the body and then insert them both into the body tissue as a unit. To facilitate this latter procedure, it may be desirable that there be some friction between the obturator 206 and the second interior passageway.

After the implantable device has been properly positioned with the adjustable element 22 located near the urethra 23 and the elastic septum in rear port element 60 located near the skin, the implantable medical device 210 is injected with a flowable material from the syringe 220. Once filling of the adjustable element 22 is complete, the obturator 206 is withdrawn from the implantable medical device 210 leaving the adjustable implantable medical device in the body tissue. Then the skin incision is closed over the rear port element 60 by means such as a suture 230 as shown in FIG. 12.

As described, one feature of this invention relates to the adjustability of the adjustable element 22 postoperatively. This adjustability is effected because the elastic septum is located remote from the adjustable element 22 but near and under the patient's skin. The rear port element 60 and the elastic septum are located by, for instance, manual palpation of the skin region and the needle of the syringe is inserted through the skin and septum so as to add or remove material from the adjustable element 22, thus increasing or decreasing the restriction of the body lumen.

Referring to FIG. 13, there is shown one embodiment of the adjustable element 22 implanted adjacent a body lumen. The adjustable element 22 is shown in an expanded state, such that it increases both localized tissue volume and passive occlusive pressure upon the body lumen. In one embodiment, the body lumen is the urethra 23 of a patient, and the patient's incontinence is treated by positioning one or more of the adjustable elements 22 of the implantable medical devices 210 adjacent the urethra 23 so as to allow the physician to adjust liquid flow resistance in the urethra 23. This is accomplished by the implantable devices coapting the patient's urethra as previously described so as to maintain a transverse cleft or slit structure of the collapsed urethra and thereby provide sufficient flow resistance, so that enough pressure is provided to maintain continence, but not so much pressure as to prevent the patient from consciously urinating.

Figure 14:
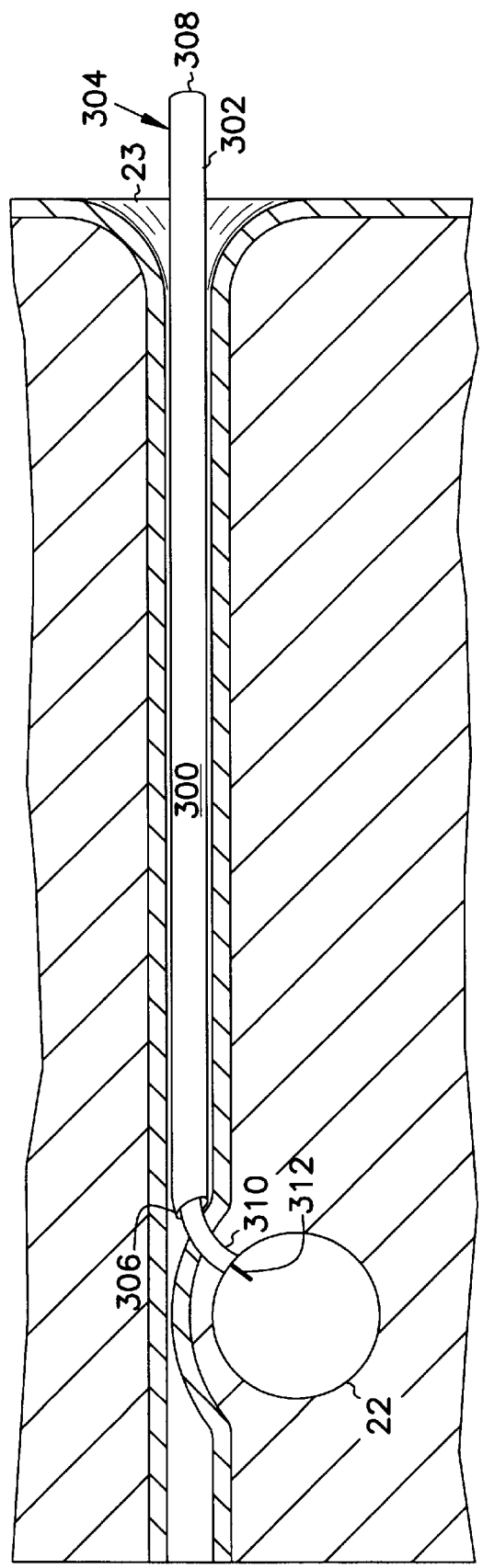
FIG. 14 is one embodiment of adjusting an implanted adjustable element.
Figure 15:
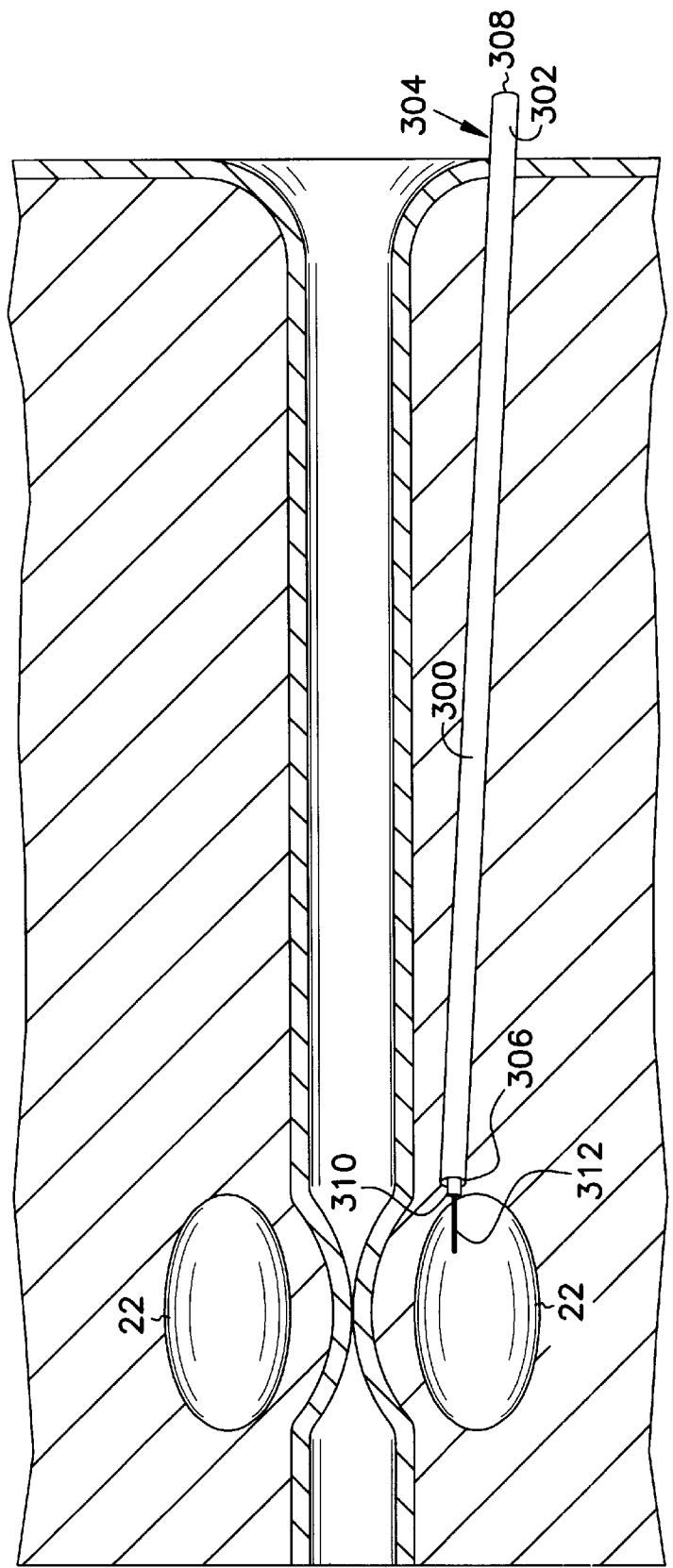
FIG. 15 is one embodiment of adjusting an implanted adjustable element.

Referring now to FIGS. 14 and 15 there is shown embodiments of postoperatively adjusting an implanted adjustable element 22. The adjustable element 22 having been implanted adjacent a body lumen within a patient, is first located within the tissues of the patient. In one embodiment, locating the adjustable element 22 is accomplished using fluoroscopy, x-ray, or ultrasound visualization techniques as are known in the art. Once the adjustable element has been located within the tissue of the patient, the physician then proceeds to establish fluid communication with the adjustable element 22. In FIG. 14 one adjustable element 22 having generally a spherical configuration is shown positioned adjacent a body lumen, such as a urethra or a ureter proper, of a patient. Alternatively, FIG. 15 shows an additional embodiment where two adjustable elements 22 each having a configuration that is generally an elongate body having semi-spherical end portions.

In one embodiment, fluid communication is established with the adjustable element by first inserting a catheter structure 300 into the urethra of the patient. In one embodiment, the catheter structure 300 has an elongate body 302 proximal end 304 and a distal end 306. The catheter structure 300 includes a fluid passageway extending longitudinally within the catheter structure 300 from an inlet port 308 at the proximal end 304 to a outlet port 310 at the distal end 306. In one embodiment, a hollow non-coring needle 312 is coupled to the outlet port 310. In an additional embodiment, the fluid passageway housed within the elongate body 302 of the catheter structure 300 moves longitudinally within the elongate body 302 to allow the hollow non-coring needle 312 coupled to the outlet port 310 to, in one position, extend beyond the distal end 306 of the elongate body 302, and in another position to be housed completely within the elongate body 302 of the catheter structure 300.

In an additional embodiment, the path of the hollow non-coring needle 312 as it is extended beyond the distal end 306 of the catheter structure 300 deflects away from a plane that is generally parallel with the longitudinal axis of the elongate body 302 of the catheter structure 300. In one embodiment, this allows the hollow non-coring needle 312 to penetrate through the urethral tissue and into the continuous wall of the adjustable element 22. The hollow non-coring needle 312 is then advance into the chamber of the adjustable element 22 at which point the physician adjusts the volume of the adjustable element 22. In one embodiment, the volume of the adjustable element is adjusted by passing fluid and/or particles through the hollow non-coring needle to adjustably contract or expand the adjustable element 22 due to fluid volume introduced into the chamber.

FIG. 15 shows an alternative embodiment for adjusting the adjustable element 22, where the catheter structure 300 is first inserted through the tissues of the patient. The distal end of the catheter structure 300 is then aligned with the outside surface of the adjustable element 22 and the hollow non-coring needle 312 is advance through the continuous wall of the adjustable element and into the chamber to allow the adjustable element to be either expanded or contracted by passing fluid, particles and/or hydrophilic polymer through the hollow non-coring needle 312 as previously described.

In an additional embodiment, the elongate body 302 of the catheter structure 300 acts as a needle stop to limit the depth to which the needle is allow to penetrate the implanted adjustable element 22. In an additional embodiment, the outer surface 32 of the adjustable element is secured to the catheter structure 300 during the insertion of the hollow non-coring needle 312 into the adjustable element 22. In one embodiment, a suction passageway extends longitudinally within the elongate body 302 to allow the distal end 306 of the catheter structure 300 to be secured to the outer surface 32 of the adjustable element 22 by a negative or vacuum pressure applied through the suction passageway. Once the catheter structure 300 is secured to the adjustable element 22, the hollow non-coring needle 312 is extended from the catheter structure 300 to pierce the continuous wall of the adjustable element 22 and allow for its volumetric adjustment.

We claim:

1. An implantable device, comprising:

an expandable element made of a single membrane enclosing a volume, the expandable element adapted to contain a flowable material and shaped to provide increased tissue volume adjacent a body lumen, the membrane adapted to self-sealing punctures made to introduce and withdraw the flowable material;

wherein the expandable element expands upon introduction of flowable material into the membrane and contracts upon withdrawal of flowable material from the membrane, and where the expandable element is adjustable in size by adjusting an amount of flowable material in the membrane to control coaptation of the body lumen.

2. The implantable device of claim 1, where the membrane is made of a resilient material.

3. The implantable device of claim 1, where the expandable element expands to a predetermined shape.

4. The implantable device of claim 1, where the membrane includes a mesh.

5. The implantable device of claim 1, where a self-sealing material is applied to an inner surface of the membrane.

6. The implantable device of claim 1, the membrane comprising one or more reinforcing structures.

7. The implantable device of claim 6, where the one or more reinforcing structures is constructed using one or more materials, the materials comprising polyester, nylon, polypropylene, or polytetrafluoroethylene.

8. The implantable device of claim 6, where the membrane comprises a porous polymer structure permeable to a fluid, and a hydrophilic polymer substantially encapsulated in the membrane, where the hydrophilic polymer absorbs fluid to expand the expandable element.

9. The implantable device of claim 8, where the expandable element expands or contracts by introducing or removing the hydrophilic polymer from the membrane.

10. The implantable device of claim 8, where the hydrophilic polymer is one or more of hyaluronic acid, polyvinylpyrrolidone, polyethylene glycol, carboxy methyl cellulose, or hyaluronic acid.

11. The implantable device of claim 8, where the hydrophilic polymer has a particulate structure having an average diameter that is greater than an average diameter of pores of the porous polymer structure.

12. The implantable device of claim 6, where the flowable material introduced into the membrane includes particles having diameters greater than openings through the one or more reinforcing structures.

13. The implantable device of claim 8, where the porous polymer structure has openings that are less than or equal to 200 micrometers.

14. The implantable device of claim 1, where the membrane is constructed of a biocompatible resiliently elastomeric polymer or polymer blend.

15. The implantable device of claim 14, where the biocompatible resiliently elastomeric polymer or polymer blend is selected from the group comprising one or both of polyurethane or silicone.

16. The implantable device of claim 1, where the expandable element has an outer surface generally defining a sphere.

17. The implantable device of claim 1, where the expandable element has an outer surface generally defining an elongate body having semi-spherical end portions.

18. The implantable device of claim 1, where a detectable marker is imbedded in the membrane of the adjustable element.

19. The implantable device of claim 1, wherein the membrane is connected to a conduit at a first end, the conduit having a second end connected to a port, providing fluid communication between the port and the membrane, such that flowable material introduced into the port is passed into the membrane.

20. The implantable device of claim 19, where the conduit comprises a passageway extending longitudinally and of diameter to receive an elongate probe member.

21. The implantable device of claim 17, where the rear port is adapted for sealing to contain flowable material within the implantable device.

22. The implantable device of claim 21, where the rear port comprises a septum.

23. An implantable device assembly adapted for being surgically implanted into body tissue of a patient adjacent to a body lumen for collapsing the body lumen, the assembly comprising;

an implantable device adapted for being surgically implanted into the tissue adjacent to the body lumen, the implantable device including an adjustable element, a tubular elongate body, and a rear port element;

the adjustable element having a continuous wall, including an inner surface defining a chamber;

the tubular elongate body, having a peripheral surface, a proximal end and a distal end, where the peripheral surface is connected to and sealed to the adjustable element, the tubular elongate body including a first interior passageway and a second interior passageway, the first interior passageway extending longitudinally in the tubular elongate body from a first port at the proximal end to a second port in fluid communication with the chamber of the implantable device for adjustably expanding or contracting the expandable element by applied fluid volume introduced through the first port, and the second interior passageway extending longitudinally in the tubular elongate body from a proximal opening through the peripheral surface positioned between the proximal and the distal end to a distal opening through the distal end of the tubular elongate body, the second interior passageway being of sufficient diameter to receive and guide an obturator for the insertion of the implantable device into a human body;

the rear port element coupled to the proximal end of the tubular elongate body, the rear port element including a cavity in fluid communication with the first port of the first interior passageway; and a fluid source adapted to be releasably connected to the rear port element, where the adjustable element expands or contracts due to fluid volume introduced into the cavity of the rear port element from the fluid source to at least partially and adjustably restrict the body lumen.

24. The implantable device assembly of claim 23, where the rear port element has an elastic septum and the fluid source is a syringe having a hollow non-coring needle, where the hollow non-coring needle is inserted through the elastic septum and fluid from the syringe is introduced into or extracted from the cavity in the rear port element to expand or contract the adjustable element.

25. A method for adjustably restricting a body lumen in a patient, comprising:

locating an adjustable element previously implanted adjacent a body lumen, where the adjustable element has a volume;

establishing fluid communication with the adjustable element; and adjusting the volume of the adjustable element to affect coaptation of the body lumen.

26. The method of claim 25, wherein the adjustable element has a continuous wall, including an inner surface defining a chamber, and wherein establishing fluid communication includes inserting a hollow needle into the chamber of the adjustable element and adjusting includes passing fluid through the hollow needle to adjustably contract or expand the adjustable element due to fluid volume introduced into the chamber or removed from the chamber.

27. The method of claim 26, wherein passing fluid through the hollow needle establishing fluid communication includes passing a suspension of particles suspended in the fluid through the hollow needle to adjustably contract or expand the adjustable element by introducing or removing a volume of the suspension from the chamber.

28. The method of claim 25, wherein the adjustable element has a continuous wall, including an inner surface and an outer surface, where the inner surface defines a chamber and at least a portion of the continuous wall has a porous polymer structure that allows the movement of water between the outer surface and the inner surface, and wherein adjusting includes encapsulating a hydrophilic polymer substantially in the chamber, where the hydrophilic polymer absorbs water to expand the implantable device.

29. The method of claim 28, wherein establishing fluid communication includes:

inserting a hollow needle into the chamber of the adjustable element; and passing a hydrophilic polymer through the hollow needle to adjustably contract or expand the adjustable element by introducing or removing the hydrophilic polymer from the chamber.

30. The method of claim 25, where the adjustable element is generally spherical and where one or more of the adjustable elements are implanted adjacent a urethra.

31. The method of claim 25, where the adjustable element is generally spherical and where one or more of the adjustable elements are implanted adjacent a ureter.

32. The method of claim 25, where the volume of the adjustable element is postoperatively adjusted.

33. A method for restricting a body lumen in a patient, comprising the steps of:

inserting an obturator into body tissue of a patient to locate a portion of the obturator adjacent the body lumen to be restricted;

providing an implantable device adapted to be surgically implanted into the body tissue adjacent to the body lumen, the implantable device including an adjustable element having a volume, a tubular elongate body, and a rear port element;

moving the implantable device along the obturator to position the adjustable element adjacent the body lumen;

passing a fluid from a source through the rear port element, so as to alter the volume of the adjustable element sufficient to at least partially restrict the body lumen, then removing the source;

removing the obturator from the body tissue; and positioning the rear port element in the body tissue.

34. The method of claim 33, where in the step of moving, the adjustable element is positioned adjacent a urethra.

35. The method of claim 33, where two or more of the implantable devices are implanted within the body tissue adjacent a urethra.

36. The method of claim 25, wherein the adjustable element is filled through the urethral wall or adjacent the urethral wall.

* * * * *

UNITED STATES PATENT AND TRADEMARK OFFICE
CERTIFICATE OF CORRECTION

PATENT NO.: 5,964,806
DATED: Oct. 12, 1999
INVENTOR(S): Cook et al.

It is certified that errors appear in the above-identified patent and that said patent is hereby corrected as shown below:

In column 14, line 59 after "device" add --for controlling coaptation of a body lumen--.

In column 15, line 24 after "element" add --and thereby making said membrane porous and self-sealing--.

In column 16, line 1 delete "the" (second occurance) and insert --a--, therefor.

In column 16, line 57 after "lumen" add --in a separate procedure--.

Signed and Sealed this

Thirteenth Day of February, 2001

Attest:

NICHOLAS P. GODICI

Attesting Officer

Acting Director of the United States Patent and Trademark Office